United States Patent
Aoki

(10) Patent No.: US 11,833,296 B2
(45) Date of Patent: Dec. 5, 2023

(54) GAS MONITORING APPARATUS AND SYSTEM FOR ARTIFICIAL VENTILATION

(71) Applicant: NIHON KOHDEN CORPORATION, Tokyo (JP)

(72) Inventor: Toshiki Aoki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 416 days.

(21) Appl. No.: 16/014,564

(22) Filed: Jun. 21, 2018

(65) Prior Publication Data
US 2018/0369520 A1 Dec. 27, 2018

(30) Foreign Application Priority Data

Jun. 27, 2017 (JP) ................................. 2017-125243
Jun. 14, 2018 (JP) ................................. 2018-113459

(51) Int. Cl.
*A61M 16/00* (2006.01)
*A61B 5/00* (2006.01)

(52) U.S. Cl.
CPC .... *A61M 16/0003* (2014.02); *A61M 16/0096* (2013.01); *A61M 16/024* (2017.08);
(Continued)

(58) Field of Classification Search
CPC ............ A61M 16/0003; A61M 16/024; A61M 16/0096; A61M 2230/432;
(Continued)

(56) References Cited

U.S. PATENT DOCUMENTS 4,421,113 A * 12/1983 Gedeon ............... A61M 16/024
128/204.18
4,520,812 A * 6/1985 Freitag .............. A61M 16/0096
128/207.14
(Continued)

FOREIGN PATENT DOCUMENTS

EP 2138199 A1 * 12/2009 ............ A61M 16/08
EP 2 682 054 A1 1/2014
(Continued)

OTHER PUBLICATIONS

European Patent Office Communication pursuant to Article 94(3) EPC issued in European Patent Application No. 18 179 274 dated Jun. 21, 2019.
(Continued)

*Primary Examiner* — Elliot S Ruddie
(74) *Attorney, Agent, or Firm* — Pearne & Gordon LLP

(57) ABSTRACT

A gas monitoring system for artificial ventilation includes: a sensor that is configured to produce a signal corresponding to a concentration of a predetermined gas in a portion which is in a respiratory circuit of an artificial ventilator, and through which both an inspiratory gas and an expiratory gas pass; a displaying apparatus that is communicable with the sensor; a processor; and a memory that is configured to store a command which is readable by the processor. When, during high-frequency oscillatory ventilation performed by the artificial ventilator, the command is executed by the processor, the processor is to configured to calculate a measurement value of the concentration based on the signal, and is configured to display at least one of a waveform corresponding to the signal and the measurement value on the displaying apparatus.

23 Claims, 4 Drawing Sheets

(52) U.S. Cl.
CPC ...... *A61B 5/725* (2013.01); *A61M 2016/0036* (2013.01); *A61M 2230/432* (2013.01)

(58) Field of Classification Search
CPC ........... A61M 2016/0036; A61B 5/725; A61B 5/083–0836
USPC .................................................. 128/204.21
See application file for complete search history.

(56) References Cited

U.S. PATENT DOCUMENTS

| | | | | |
|---|---|---|---|---|
| 4,859,858 | A * | 8/1989 | Knodle | G01N 21/3504 250/493.1 |
| 5,423,313 | A | 6/1995 | Olsson et al. | |
| 6,390,092 | B1 * | 5/2002 | Leenhoven | A61M 16/0096 128/204.23 |
| 6,446,629 | B1 | 9/2002 | Takaki et al. | |
| 2004/0050142 | A1 * | 3/2004 | Hok | G01N 29/38 73/23.21 |
| 2007/0261698 | A1 * | 11/2007 | Palatnik | G01N 21/3504 128/207.14 |
| 2008/0161710 | A1 * | 7/2008 | Gunneson | A61M 16/021 600/532 |
| 2010/0249631 | A1 * | 9/2010 | Aoki | A61B 5/0836 600/532 |
| 2010/0317933 | A1 | 12/2010 | Colman et al. | |
| 2010/0317986 | A1 * | 12/2010 | Colman | A61B 5/0836 600/532 |
| 2011/0040713 | A1 | 2/2011 | Colman et al. | |
| 2011/0098592 | A1 | 4/2011 | Colman et al. | |
| 2011/0302992 | A1 * | 12/2011 | Robbins | G01N 21/05 73/23.3 |
| 2012/0145152 | A1 | 6/2012 | Lain et al. | |
| 2012/0220845 | A1 * | 8/2012 | Campbell | A61M 16/0447 600/364 |
| 2013/0204099 | A1 | 8/2013 | Colman et al. | |
| 2013/0289364 | A1 | 10/2013 | Colman et al. | |
| 2014/0155775 | A1 | 6/2014 | Colman et al. | |
| 2014/0155776 | A1 | 6/2014 | Colman et al. | |
| 2016/0174907 | A1 | 6/2016 | Colman et al. | |
| 2016/0345843 | A1 | 12/2016 | Colman et al. | |
| 2017/0143277 | A1 * | 5/2017 | Lisogurski | A61B 5/14551 |
| 2017/0296095 | A1 | 10/2017 | Colman et al. | |
| 2018/0070859 | A1 | 3/2018 | Colman et al. | |

FOREIGN PATENT DOCUMENTS

| | | |
|---|---|---|
| JP | S58-500236 A | 2/1983 |
| JP | S58-180164 A | 10/1983 |
| JP | 2000-042109 A | 2/2000 |
| JP | 2010-514472 A | 5/2010 |
| JP | 2011-522583 A | 8/2011 |
| WO | 2009-144731 A2 | 12/2009 |

OTHER PUBLICATIONS

Extended European Search Report issued in Patent Application No. EP 18 17 9274 dated Nov. 7, 2018.
Japanese Office Action dated Jan. 18, 2022 issued in Japanese Patent Application No. 2018-113459.
Japanese Office Action dated Aug. 9, 2022 issued in Japanese Patent Application No. 2018-113459.
Japanese Office Action issued in Japanese Patent Application No. 2018-113459.
Japanese Office Action dated Aug. 8, 2023 issued in Japanese Patent Application No. 2018-113459.

* cited by examiner

GAS MONITORING APPARATUS AND SYSTEM FOR ARTIFICIAL VENTILATION

CROSS-REFERENCE TO RELATED APPLICATION(S)

This application is based upon and claims the benefit of priority from prior Japanese patent application No. 2017-125243, filed on Jun. 27, 2017, and Japanese patent application No. 2018-113459, filed on Jun. 14, 2018, the entire contents of which are incorporated herein by reference.

BACKGROUND

The presently disclosed subject matter relates to a gas monitoring apparatus for artificial ventilation which is communicable with a sensor that produces a signal corresponding to the concentration of a respiratory gas in a respiratory circuit of an artificial ventilator. The presently disclosed subject matter relates also to a gas monitoring system for artificial ventilation which includes a displaying apparatus that is communicable with the sensor.

As an artificial ventilation method, the low-frequency ventilation method and the high-frequency oscillatory ventilation method are available. The low-frequency ventilation method is a technique in which oxygen corresponding to the usual respiratory displacement volume is forcibly supplied to the lungs of the patient at the usual respiratory frequency (about 10 to 20 times per minute). The high-frequency oscillatory ventilation method is a technique in which an oscillatory air pressure in which a positive pressure and a negative pressure are repeated at a high frequency is generated, and oxygen is supplied at a ventilation volume (ejection volume) that is smaller than the anatomical dead space, to the lungs of the patient. The term "high-frequency oscillatory" means an oscillation at a frequency which is higher than the usual respiratory frequency, or, for example, an oscillation of 10 to 15 Hz. For example, JP-A-2000-042109 discloses an artificial ventilator in which the high-frequency oscillatory ventilation method is employed.

The high-frequency oscillatory ventilation method does not involve forcible supply of oxygen to the lungs, and therefore it is a method in which lung damages due to pressure variation can be suppressed. In the method, on the other hand, it is impossible to obtain the respiration mode of expiration/inspiration, which can be obtained in the low-frequency ventilation method, and hence the end-tidal carbon dioxide concentration cannot be acquired. In the high-frequency oscillatory ventilation method, as a result, it is impossible to continuously monitor the ventilation state (the state of the lungs) of the patient based on the concentration.

When the high-frequency oscillatory ventilation method is performed, therefore, the carbon dioxide concentration is acquired through the blood gas measurement or a measurement using a transdermal sensor. However, the blood gas measurement requires to invasive blood sampling, and a measurement using a transdermal sensor involves risks of skin damage and low-temperature burn.

SUMMARY

The presently disclosed subject matter may provide a gas monitoring apparatus for artificial ventilation and a gas monitoring system for artificial ventilation which enable the ventilation state of a patient during implementation of the high-frequency oscillatory ventilation method, to be continuously monitored while reducing the burden on the patient.

The gas monitoring system for artificial ventilation may comprise: a sensor that is configured to produce a signal corresponding to a concentration of a predetermined gas in a portion which is in a respiratory circuit of an artificial ventilator, and through which both an inspiratory gas and an expiratory gas pass; a displaying apparatus that is communicable with the sensor; a processor; and a memory that is configured to store a command which is readable by the processor, wherein, when, during high-frequency oscillatory ventilation performed by the artificial ventilator, the command is executed by the processor, the processor is configured to calculate a measurement value of the concentration based on the signal, and is configured to display at least one of a waveform corresponding to the signal and the measurement value on the displaying apparatus.

The gas monitoring apparatus for artificial ventilation communicable with a sensor that is configured to produce a signal corresponding to a concentration of a predetermined gas in a portion which is in a respiratory circuit of an artificial ventilator, and through which both an inspiratory gas and an expiratory gas pass, may comprise: a displaying section; a processor; and a memory that is configured to store a command which is readable by the processor, wherein, when, during high-frequency oscillatory ventilation performed by the artificial ventilator, the command is executed by the processor, the processor is configured to calculate a measurement value of the concentration based on the signal, and is configured to display at least one of a waveform corresponding to the signal and the measurement value on the displaying section.

DETAILED DESCRIPTION OF EXEMPLARY EMBODIMENTS

Figure 1:
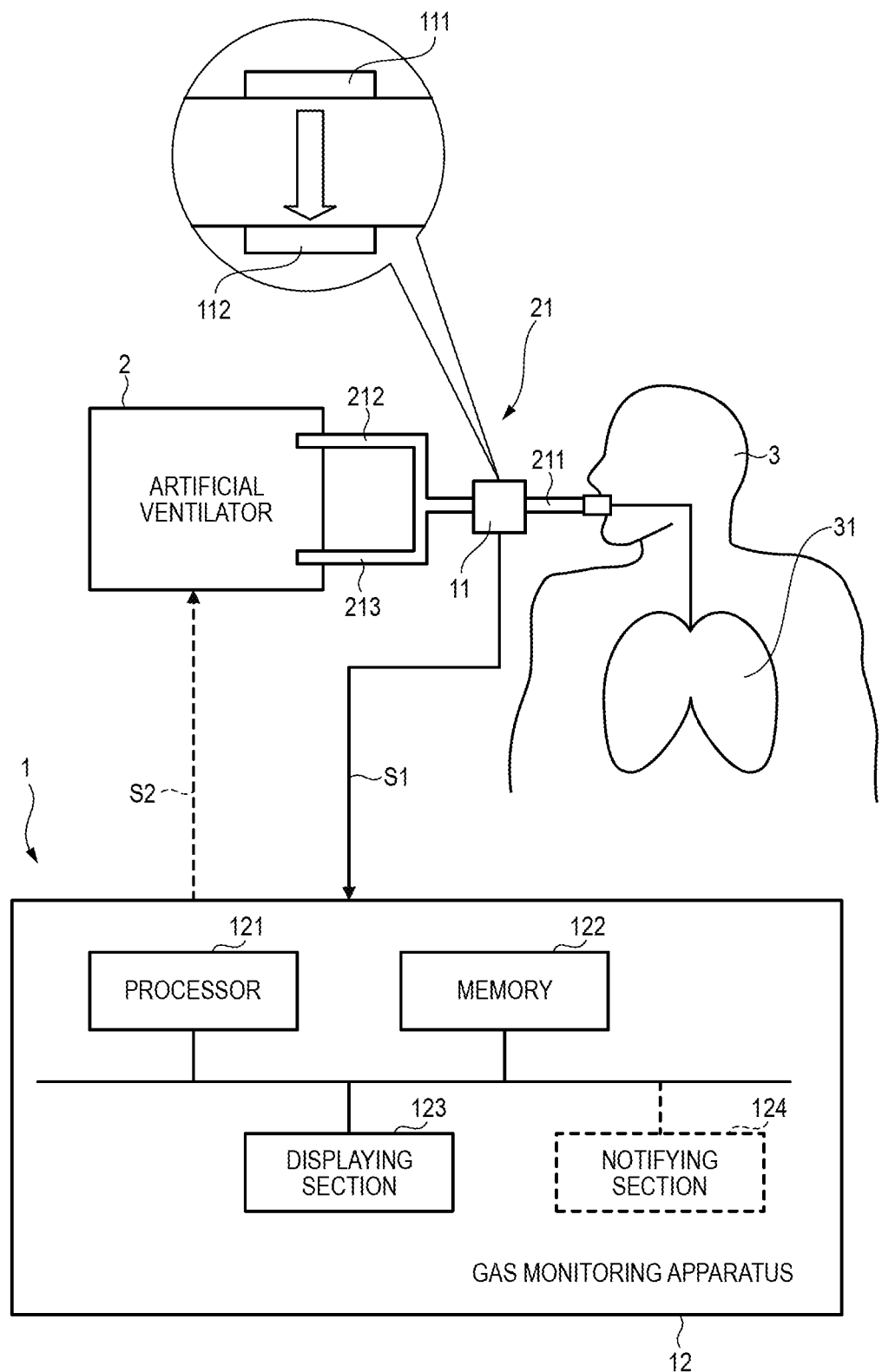
FIG. 1 is a diagram showing a gas monitoring system for artificial ventilation of an embodiment.

Hereinafter, an embodiment will be described in detail with reference to the accompanying drawings. FIG. 1 shows the configuration of a gas monitoring system 1 of the embodiment. In FIG. 1, in order to make the components to have a recognizable size, their scales are appropriately changed.

The gas monitoring system 1 can operate in cooperation with an artificial ventilator 2. The artificial ventilator 2 is configured so as to perform at least high-frequency oscillatory ventilation. The configuration for enabling high-frequency oscillatory ventilation to be performed is a related art, and therefore its detailed description is omitted.

The artificial ventilator 2 includes a respiratory circuit 21. The respiratory circuit 21 includes a common circuit section 211, an inspiratory circuit section 212, and an expiratory circuit section 213.

One end of the common circuit section 211 is connected to the lungs 31 of the patient 3 by airtightly fixing the section to the mouth of the patient 3. The other end of the common circuit section 211 is bifurcated into the inspiratory circuit section 212 and the expiratory circuit section 213. The inspiratory circuit section 212 is a portion for sending an inspiratory gas for artificial ventilation toward the common circuit section 211. The expiratory circuit section 213 is a portion for discharging an expiratory gas supplied from the patient 3 toward the atmosphere. Namely, the common circuit section 211 is a portion through which both the inspiratory gas and the expiratory gas pass.

The gas monitoring system 1 includes a sensor 11. The sensor 11 is placed in the common circuit section 211 of the artificial ventilator 2. The sensor 11 is configured so as to produce a signal S1 corresponding to the concentration of carbon dioxide in the common circuit section 211. Carbon dioxide is an example of the predetermined gas.

Specifically, the sensor 11 includes a light emitter 111 and a light detector 112. The light emitter 111 is configured so as to emit an infrared light beam of constant intensity toward the common circuit section 211. The light detector 112 is located so as to receive the infrared light beam which has passed through the common circuit section 211. Since an infrared light beam is absorbed by carbon dioxide, the intensity of the light beam which is received by the light detector 112 is changed in accordance with the concentration of carbon dioxide in the common circuit section 211. The light detector 112 is configured so as to produce the signal S1 corresponding to the intensity of the received light beam. The signal S1 is a DC signal.

In the embodiment, the response time of the light detector 112 is 55 milliseconds or shorter. The response time is defined as a time period extending from a timing when an output signal which is produced by an input of a gas having a step-like reference waveform rises, and a value corresponding to 10% of the maximum amplitude of the signal is obtained, to that when a value corresponding to 90% is obtained.

The gas monitoring system 1 further includes a gas monitoring apparatus 12. The gas monitoring apparatus 12 can communicate with the sensor 11. In the embodiment, the term in "can communicate" means a state where at least one of transmission and reception of a signal or data is possible. In this case, subjects participating in communication may be wired or wirelessly connected.

The gas monitoring apparatus 12 includes a processor 121 and a memory 122. The memory 122 stores a command which can be executed by the processor 121. Examples of the processor 121 are a CPU and an MPU. Examples of the memory 122 are a ROM and a RAM.

The gas monitoring apparatus 12 further includes a displaying section 123. Namely, the gas monitoring apparatus 12 functions also as a displaying apparatus.

Figure 2:
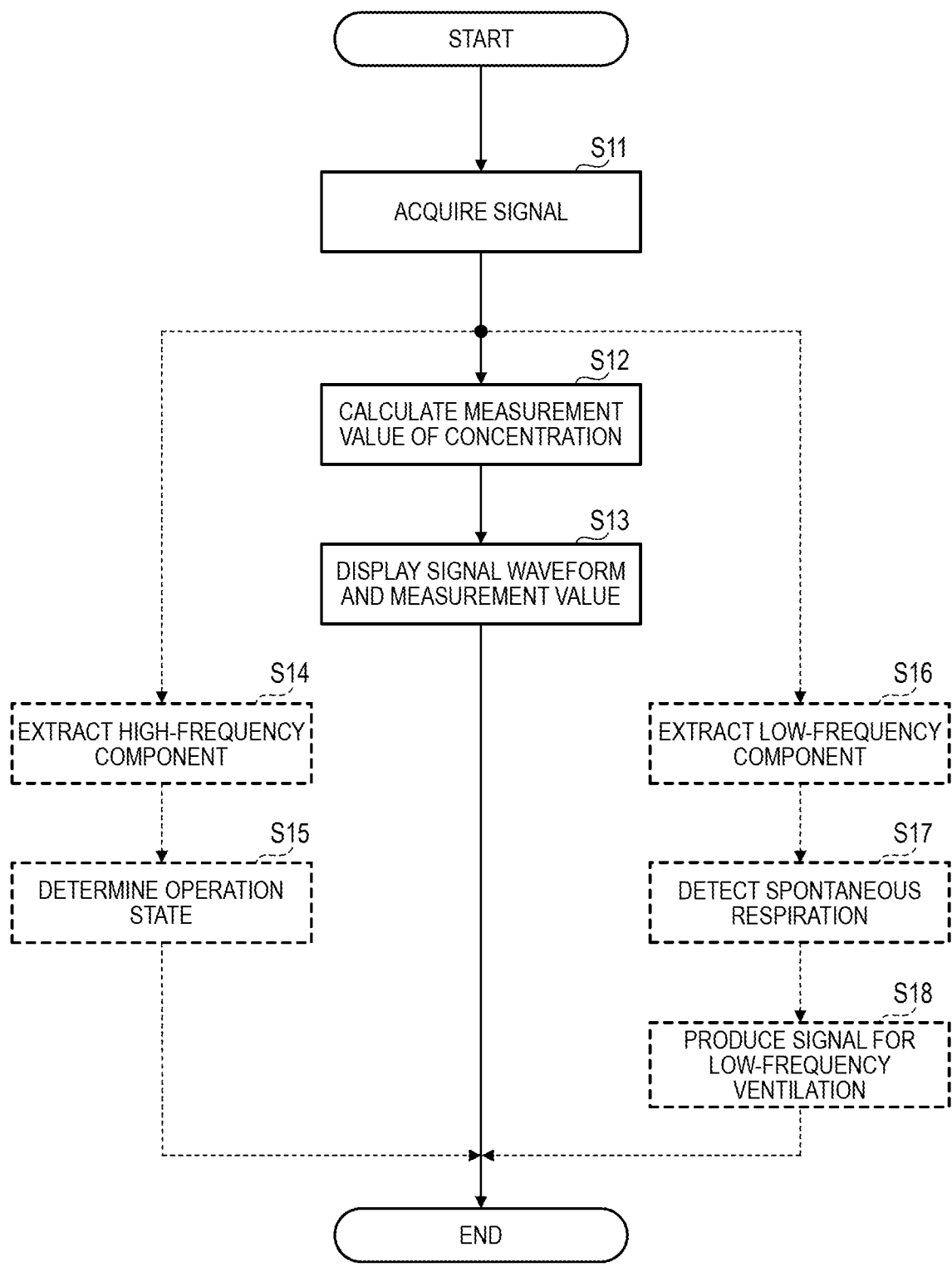
FIG. 2 is a flowchart showing an operation example of the gas monitoring system of FIG. 1.

In the case where the artificial ventilator 2 performs high-frequency oscillatory ventilation, when the command stored in the memory 122 is executed by the processor 121, the process shown in FIG. 2 is executed by the gas monitoring apparatus 12.

First, the signal S1 produced by the light detector 112 of the sensor 11 is acquired (step S11). Next, the measurement value of the carbon dioxide concentration in the common circuit section 211 is calculated based on the signal S1 (step S12).

Figure 3A:
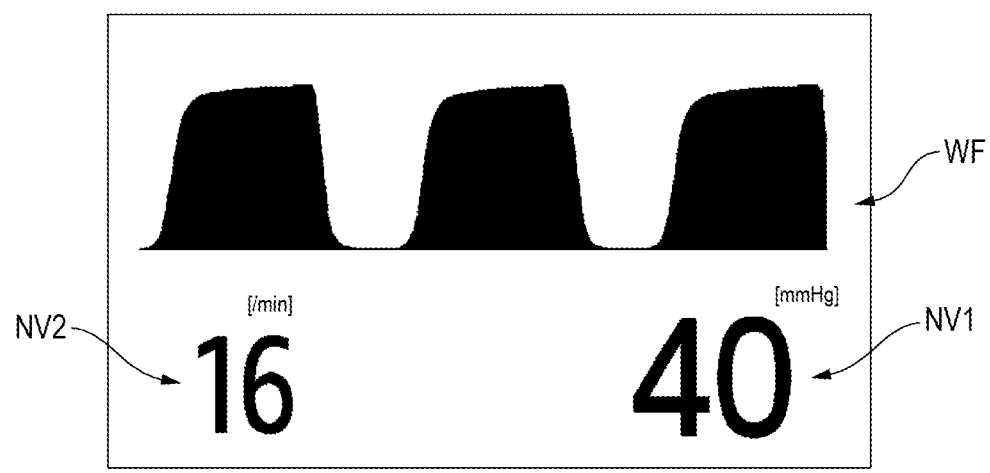
FIGS. 3A, 3B and 3C are views showing operation examples of the gas monitoring system of FIG. 1.
Figure 3B:
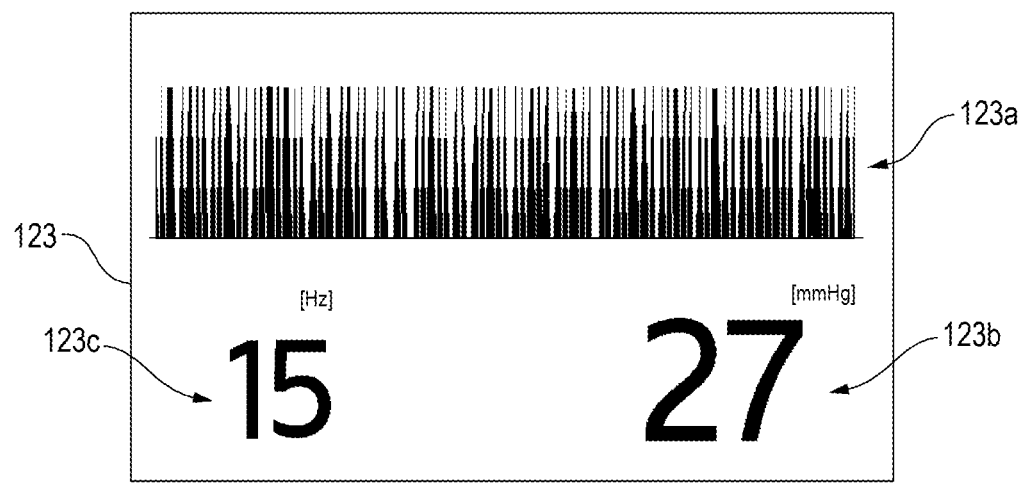

As exemplified in FIG. 3B, a waveform 123a corresponding to the signal S1, and the calculated measurement value 123b of the carbon dioxide concentration are displayed on the displaying section 123 (step S13). In the example, the measurement value 123b indicates 27 mmHg.

FIG. 3A shows a display example which is a comparison example. The waveform WF shows the temporal change of the carbon dioxide concentration in the common circuit section 211 in the case where the low-frequency ventilation method is performed. A respiration mode in which the numerical value is increased by the expiration, and decreased by the inspiration clearly appears. The numerical value NV1 indicates the carbon dioxide concentration. For example, the concentration of carbon dioxide corresponding to the maximum value of the waveform WF is displayed as the numerical value NV1. The numerical value NV2 indicates the respiration rate per minute. The numerical value NV2 is specified based on the cycle of the waveform WF.

By contrast, the waveform 123a which is obtained in the high-frequency oscillatory ventilation method reflects the temporal change of the carbon dioxide concentration due to the oscillating air pressure in the common circuit section 211. Therefore, the waveform fails to exhibit a clear respiration mode. Consequently, the measurement value 123b of the carbon dioxide concentration is calculated by acquiring the moving average of a plurality of peak values of the signal S1 contained in a predetermined period of time, or by identifying the maximum value of a plurality of peak values of the signal S1 contained in a predetermined period of time.

The inventor of this application has found that, when the sensor 11 having the above-described specification is placed in the common circuit section 211, a measurement value of the carbon dioxide concentration according to the actual condition of the patient 3 can be obtained by a relatively simple calculation process such as the acquisition of the moving average or the maximum value. The waveform obtained in the high-frequency oscillatory ventilation method is often fluctuated, even if there is not spontaneous respiration. In the case where the measurement value of the carbon dioxide concentration is obtained by acquiring the moving average, the influence of noise can be reduced. In the case where the measurement value of the carbon dioxide concentration is obtained by acquiring the maximum value, the value closer to the partial pressure of the carbon dioxide in alveolus can be obtained.

According to the configuration, even during implementation of the high-frequency oscillatory ventilation method, the ventilation state of the patient 3 can be continuously monitored without using the blood gas measurement or a measurement using a transdermal sensor. In other words, during implementation of the high-frequency oscillatory ventilation method, the ventilation state of the patient 3 can be continuously monitored while reducing the burden on the patient 3.

Figure 3C:
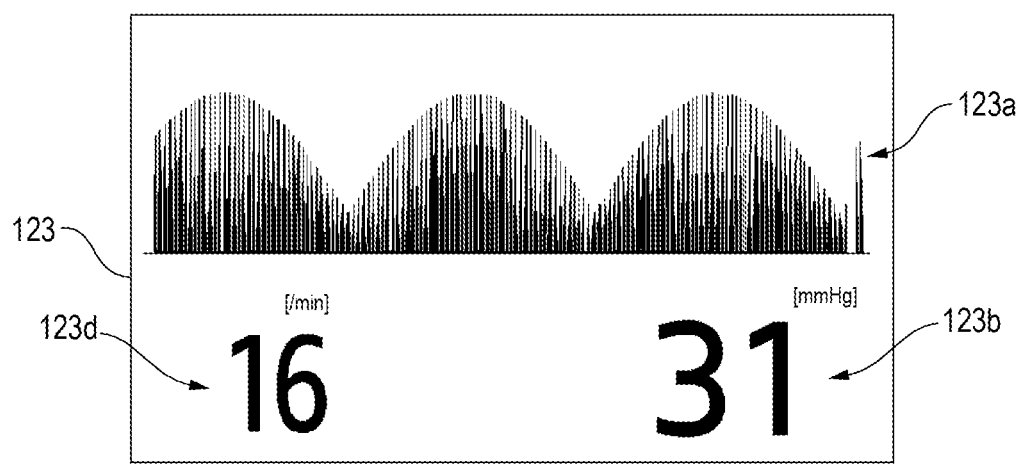

Moreover, the waveform 123a is displayed based on the signal S1 which is obtained in the common circuit section 211 that is closer to the lungs 31 of the patient 3. Therefore, the ventilation state of the patient 3 can be known more correctly and visually. For example, FIG. 3C shows an example of the waveform 123a in the case where the intensity of spontaneous respiration of the patient 3 is enhanced during implementation of the high-frequency oscillatory ventilation method. The medical person can take an appropriate countermeasure in view of visual recognition of the change of the waveform. In accordance with the degree of spontaneous respiration, for example, the medical person can consider switching from the high-frequency oscillatory ventilation method to the low-frequency ventilation method. The sensor 11 is placed in the common circuit section 211, and therefore can be used also in the low-frequency ventilation method. In switching between the high-frequency oscillatory ventilation method and the low-frequency ventilation method, in other words, it is not necessary to change the placement position of the sensor 11. This fact leads to reduction of the burdens of both the patient 3 and the medical person.

According to the above description, the measurement value 123b of the carbon dioxide concentration is calculated by acquiring the moving average of a plurality of peak values of the waveform 123a contained in the predetermined period of time. Alternatively, the measurement value 123b may be calculated by identifying the maximum value of a plurality of peak values contained in a predetermined period of time. The measurement value 123b may be calculated from a waveform in which a high-frequency component is removed by a low-pass filter.

As indicated by the broken line in FIG. 1, the gas monitoring apparatus 12 can include a notifying section 124. The processor 121 can be configured so as to, when the measurement value 123b of the carbon dioxide concentration has a value outside a range which is defined by upper and lower thresholds, cause the notifying section 124 to perform a notifying operation. In this case, the notification process is performed using at least one of visual notification, audible notification, and haptic notification. The numerical range relating to the notification is not always required to be defined by upper and lower thresholds. Only one of upper and lower thresholds may be set.

As indicated by the broken lines in FIG. 2, when the command stored in the memory 122 is executed by the processor 121 in the case where high-frequency oscillatory ventilation is performed by the artificial ventilator 2, the gas monitoring apparatus 12 can implement a process of extracting a high-frequency component from the signal S1 which is acquired in step S11 (step S14).

Specifically, a high-frequency component having a frequency which is higher than a predetermined value is extracted from the signal S1. The predetermined value is adequately determined based on the oscillation frequency of the high-frequency oscillatory ventilation. The extracting process may be performed by passing the signal through a high-pass filter circuit in which the predetermined value is set as the threshold frequency, or by applying a signal process equivalent to passage through the high-pass filter to the signal S1.

In this case, as shown in FIG. 3B, a frequency value 123c corresponding to the cycle of the extracted high-frequency component can be displayed on the displaying section 123. In the example, the frequency value 123c indicates 15 Hz.

According to the configuration, it is possible to visually determine whether the high-frequency oscillatory ventilation is normally performed or not, based on the displayed frequency value 123c. When a leak exists in a part of the respiratory circuit 21, for example, the oscillation due to high-frequency oscillatory ventilation does not sufficiently act on the common circuit section 211, and a case may arise where the desired waveform 123a cannot be obtained. Specifically, there is a case where the waveform 123a corresponding to the oscillation is not contained in the waveform 123a in association with a sufficient level. Such a situation can be known by visually checking the frequency value 123c.

In addition to or in place of the above, the gas monitoring apparatus 12 can automatically determine whether the high-frequency oscillatory ventilation is normally performed or not, based on the high-frequency component of the signal S1 which is extracted in step S14 (step S15).

If it is determined in step S15 that the high-frequency oscillatory ventilation is not normally performed, this can be notified through the notifying section 124.

In addition to or in place of this, when, as indicated by the broken lines in FIG. 2, the command stored in the memory 122 is executed by the processor 121 in the case where high-frequency oscillatory ventilation is performed by the artificial ventilator 2, the gas monitoring apparatus 12 can implement a process of extracting a low-frequency component from the signal S1 which is acquired in step S11 (step S16).

Specifically, a low-frequency component having a frequency which is lower than a predetermined value is extracted from the signal S1. The predetermined value is adequately determined based on the respiratory frequency of the patient 3. Alternatively, the extracting process may be performed by passing the signal through a low-pass filter circuit in which the predetermined value is set as the threshold frequency, or by applying to the signal S1 a signal process equivalent to passage through the low-pass filter.

Next, spontaneous respiration of the patient 3 is detected based on the low-frequency component of the signal S1 which is extracted in step S16 (step S17). If there is spontaneous respiration of the patient 3, a low-frequency component is superimposed on the signal S1. In the case where the level of the component exceeds a predetermined threshold, it can be determined that there is spontaneous respiration of the patient 3. When a frequency analysis is performed as described above, detection of spontaneous respiration can be automated.

As described with reference to FIG. 3C, when there is spontaneous respiration of the patient 3, a low-frequency component is superimposed also on the waveform 123a displayed on the displaying section 123. However, a waveform change caused by the superimposition is not always noticeable as in the illustrated example. When the frequency analysis is used as described above, spontaneous respiration of the patient 3 can be automatically detected without depending on the visual check of the waveform 123a.

If spontaneous respiration of the patient 3 is detected in step S17, this can be notified through the notifying section 124. In addition to or in place of the above, as shown in FIG. 3C, the respiration rate 123d per minute of the patient 3 is displayed on the displaying section 123 based on the cycle of the extracted low-frequency component. In the example, the respiration rate 123d indicates 16 times per minute.

As indicated by the broken line in FIG. 1, the gas monitoring apparatus 12 and the artificial ventilator 2 can communicate with each other. In this case, when spontaneous respiration of the patient 3 is detected in step S17 of FIG. 2, the gas monitoring apparatus 12 can produce a signal S2 for causing the artificial ventilator 2 to operate according the low-frequency ventilation method (step S18 of FIG. 2). When the signal S2 is input to the artificial ventilator 2, the artificial ventilator 2 aborts the operation based on the high-frequency oscillatory ventilation method, and begins an operation based on the low-frequency ventilation method. A display in a mode which is exemplified in FIG. 3A is performed on the displaying section 123.

According to the configuration, switching which is performed in accordance with the level of spontaneous respiration of the patient 3, and by which the high-frequency oscillatory ventilation method is changed to the low-frequency ventilation method can be automated.

In the case where only the process of S16 to S18 shown in FIG. 2 is to be executed, the sensor 11 is not always required to have the above-described specification.

There is a case where, during implementation of high-frequency oscillatory ventilation, sustained inflation (S1) is performed. Sustained inflation is a procedure in which the oscillation of the air pressure is temporarily stopped, and the airway pressure is forcibly raised to inflate the lungs. Immediately after the end of sustained inflation, a respiratory gas having a relatively high carbon dioxide concentration is discharged from the depths of the lungs. The concentration value is a feature value which can function as an index showing the ventilation state of the patient.

Figure 4A:
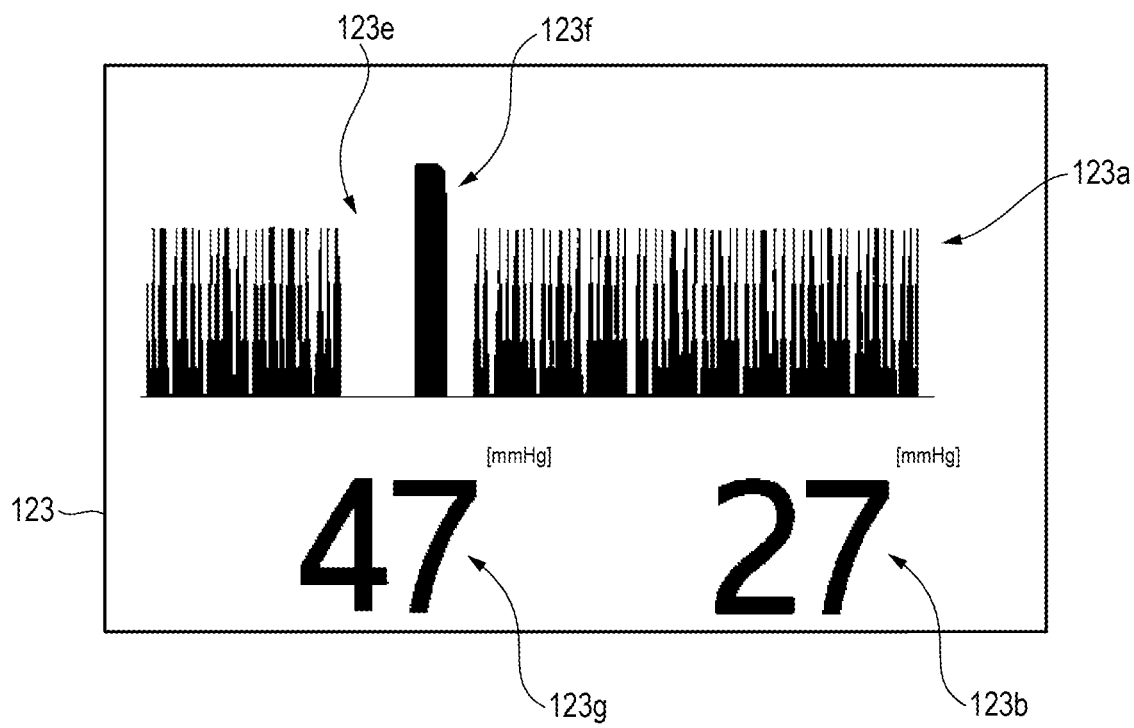
FIGS. 4A and 4B are views showing operation examples of the gas monitoring system of FIG. 1.

FIG. 4A shows an operation example of the gas monitoring apparatus 12 in the case where above-described sustained inflation is performed. In the displaying section 123, the zone 123e indicates a period of time when sustained inflation is performed. The determination that sustained inflation is performed may be conducted by acquiring information indicative of this from the artificial ventilator 2, or based on a fact that the state where the amplitude of the waveform 123a is zero is continued for a predetermined period of time or longer.

As apparent from a waveform 123f, the carbon dioxide concentration is steeply raised immediately after the end of sustained inflation. A feature value 123g is displayed based on the waveform 123f. In the example, the feature value 123g indicates 47 mmHg. The feature value 123g may be calculated by acquiring the moving average of a plurality of peak values of the waveform 123f contained in a predetermined period of time, or by identifying the maximum value of a plurality of peak values of the waveform 123f contained in a predetermined period of time.

In the example, the feature value 123g is displayed separately from the measurement value 123b. Namely, the measurement value 123b and the feature value 123g can be simultaneously displayed. According to the configuration, while monitoring the measurement value 123b which is changed in real time, the feature value 123g which can function as an index showing the ventilation state of the patient can be easily known.

The simultaneous display of the measurement value 123b and the feature value 123g enables the difference between the values to be recognized, and therefore the ventilation state of the patient can be known more correctly. It is considered that the feature value 123g reflects more correctly the carbon dioxide concentration in the alveolus. In the case where the difference between the measurement value 123b and the feature value 123g is large, for example, it can be therefore assumed that the amount of a leak from an intubation tube is increased. When the difference between the measurement value 123b and the feature value 123g is known, the carbon dioxide concentration in the alveolus can be estimated from the change of the measurement value 123b.

Figure 4B:
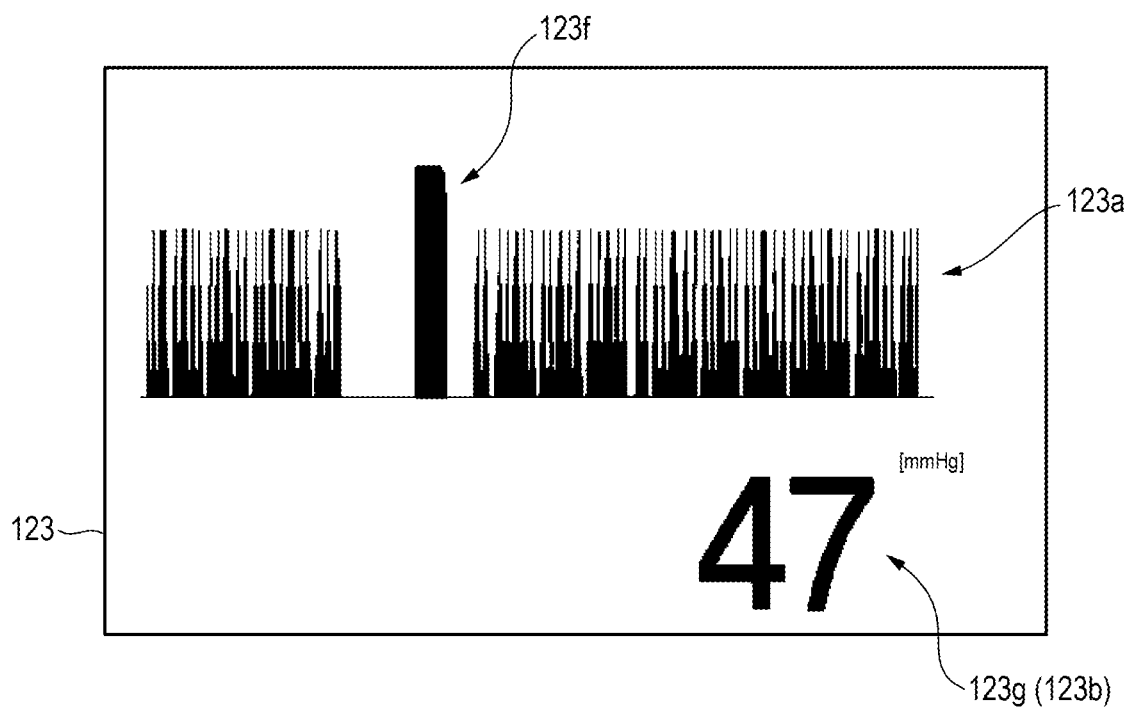

In light of the object that the grasping of the feature value 123g is facilitated, it is not always necessary to display the feature value 123a separately from the measurement value 123b. For example, a configuration may be possible where, in the case where sustained inflation is performed during display of the measurement value 123b, the feature value 123g which is identified as described above is continuously displayed for a predetermined period of time as shown in FIG. 4B.

The above-described embodiment is made for facilitating understanding of the presently disclosed subject matter, and is not intended to limit the presently disclosed subject matter. The presently disclosed subject matter may be adequately changed or improved without departing from the spirit of the presently disclosed subject matter. It is obvious that equivalents of the presently disclosed subject matter are included within the scope of the presently disclosed subject matter.

In the above-described embodiment, the concentration of carbon dioxide in the common circuit section 211 of the respiratory circuit 21 is the measurement object. When the wavelength of the light beam emitted from the light emitter 111 of the sensor 11 is adequately set, however, another gas component contained in the respiratory gas can be detected. Examples of such a gas are oxygen and nitrogen.

In the above-described embodiment, the gas monitoring apparatus 12 includes the processor 121 and the memory 122. Alternatively, the processor and memory for executing the processes which have been described with reference to FIG. 2 may be disposed in the sensor 11. In this case, in order to display the waveform 123a and the measurement value 123b, the gas monitoring apparatus 12 is requested to include at least the displaying section 123.

In the above-described embodiment, the gas monitoring apparatus 12 is independent of the artificial ventilator 2. Alternatively, at least a part of the functions of the gas monitoring apparatus 12 can be realized in the artificial ventilator 2.

In the above-described embodiment, both the waveform 123a corresponding to the signal S1 which is produced by the light detector 112, and the calculated measurement value 123b of the carbon dioxide concentration are displayed on the displaying section 123. Alternatively, the displaying section 123 may be configured so as to display only one of the waveform 123a and the measurement value 123b.

According to an aspect of the presently disclosed subject matter, in the respiratory circuit, the portion through which both the inspiratory gas and the expiratory gas pass is located in a place which is closer to the lungs of the patient. Based on the signal which is obtained in the portion, a waveform is displayed on the displaying apparatus or the displaying section. Therefore, the ventilation state of the patient can be known more correctly and visually. In the case where the intensity of spontaneous respiration of the patient is enhanced during implementation of the high-frequency oscillatory ventilation method, for example, the waveform displayed on the displaying apparatus or the displaying section is changed. The medical person can take an appropriate countermeasure in view of visual recognition of the change. In accordance with the degree of spontaneous respiration, for example, the medical person can consider switching from the high-frequency oscillatory ventilation method to the low-frequency ventilation method. The sensor is placed in the portion of the respiratory circuit through which both the inspiratory gas and the expiratory gas pass, and therefore can be used also in the low-frequency ventilation method. In switching between the high-frequency oscillatory ventilation method and the low-frequency ventilation method, in other words, it is not necessary to change the placement position of the sensor. Moreover, the implementation of the high-frequency oscillatory ventilation method is not required to depend on the blood gas measurement or a measurement using a transdermal sensor. Therefore, the ventilation state of the patient during implementation of to the high-frequency oscillatory ventilation method can be continuously monitored while reducing the burden on the patient.

What is claimed is:

1. A gas monitoring system for artificial ventilation, the gas monitoring system comprising:
a sensor that is configured to produce a signal corresponding to a concentration of a predetermined gas in a tube in a respiratory circuit of an artificial ventilator, wherein an inspiratory gas and an expiratory gas pass both pass through the tube, the inspiratory gas passing in a first direction and the expiratory gas passing in a second direction opposite to the first direction;

a displaying apparatus that is communicable with the sensor;

a processor; and a memory that is configured to store a command which is readable by the processor, wherein, when, during high-frequency oscillatory ventilation performed by the artificial ventilator, the command is executed by the processor, the processor is configured to calculate a measurement value of the concentration based on the signal, the processor is configured to display at least one of a waveform corresponding to the signal and the measurement value on the displaying apparatus, the sensor is configured such that the sensor is located at an ex vivo portion of the tube when the respiratory circuit is connected to a patient for ventilation and the sensor is operated, the processor is configured to extract a high-frequency component having a frequency which is higher than a predetermined value, from the signal, and the processor is configured to determine if the high-frequency oscillatory ventilation satisfies a desired waveform based on the high-frequency component.

2. The gas monitoring system according to claim 1, wherein, when, during the high-frequency oscillatory ventilation performed by the artificial ventilator, the command is executed by the processor, the processor is configured to extract a low-frequency component having a frequency which is lower than a predetermined value, from the signal, and the processor is configured to detect spontaneous respiration of the patient to whom the artificial ventilator is connected, based on the low-frequency component.

3. The gas monitoring system according to claim 2, wherein, in a case where the low-frequency component satisfies a predetermined condition, the processor is configured to produce a signal for causing the artificial ventilator to perform low-frequency ventilation.

4. The gas monitoring system according to claim 1, wherein, when, during the high-frequency oscillatory ventilation performed by the artificial ventilator, the command is executed by the processor, the processor is configured to display a measurement value of the concentration which is obtained after an end of sustained inflation of the lungs, as a feature value.

5. The gas monitoring system according to claim 4, wherein, when, during the high-frequency oscillatory ventilation performed by the artificial ventilator, the command is executed by the processor, the processor is configured to display the feature value separately from the measurement value of the concentration.

6. The gas monitoring system according to claim 4, wherein determination that the sustained inflation is performed is conducted by acquiring information indicating that the sustained inflation is performed from the artificial ventilator.

7. The gas monitoring system according to claim 4, wherein determination that the sustained inflation is performed is conducted based on a state where an amplitude of the waveform zero is continued for a predetermined period of time or longer.

8. The gas monitoring system according to claim 4, wherein the processor is configured to calculate the feature value by acquiring a moving average of a plurality of peak values of the waveform contained in a predetermined period of time.

9. The gas monitoring system according to claim 4, wherein the processor is configured to calculate the feature value by acquiring a maximum value of a plurality of peak values of the waveform contained in a predetermined period of time.

10. The gas monitoring system according to claim 1, wherein the processor is configured to calculate the measurement value of the concentration by acquiring a moving average of a plurality of peak values of the signal contained in a predetermined period of time.

11. The gas monitoring system according to claim 1, wherein the processor is configured to calculate the measurement value of the concentration by acquiring a maximum value of a plurality of peak values of the signal contained in a predetermined period of time.

12. The gas monitoring system according to claim 1, wherein the processor is configured to display a frequency value corresponding to a cycle of the extracted high-frequency component on the displaying apparatus.

13. The gas monitoring system according to claim 1, wherein, when, during the high-frequency oscillatory ventilation performed by the artificial ventilator, the command is executed by the processor, the processor is configured to extract a low-frequency component having a frequency which is lower than a predetermined value, from the signal, and the processor is configured to calculate a respiration rate based on a cycle of the extracted low-frequency component.

14. The gas monitoring system according to claim 1, wherein the sensor includes:

a light emitter that is located so as to emit a light beam toward the ex vivo portion of the tube, and a light detector that is located so as to receive the light beam after passing through the ex vivo portion.

15. The gas monitoring system according to claim 1, wherein:

the respiratory circuit includes an inspiratory circuit section, and an expiratory circuit section, one end of the tube being bifurcated into the inspiratory circuit section and the expiratory circuit section, and the sensor is located at the ex vivo portion of the tube.

16. The gas monitoring system according to claim 1, wherein the sensor includes a light emitter configured so as to emit a light beam toward the tube and a light detector configured so as to produce the signal corresponding to intensity of the received light beam, wherein a response time of the light detector is 55 milliseconds or shorter.

17. A gas monitoring apparatus for artificial ventilation, the gas monitoring apparatus communicable with a sensor that is configured to produce a signal corresponding to a concentration of a predetermined gas in a tube in a respiratory circuit of an artificial ventilator, wherein an inspiratory gas and an expiratory gas both pass through the tube, the inspiratory gas passing in a first direction and the expiratory gas passing in a second direction opposite to the first direction, the gas monitoring apparatus comprising:
  a displaying section;
  a processor; and
  a memory that is configured to store a command which is readable by the processor, wherein,
  when, during high-frequency oscillatory ventilation performed by the artificial ventilator, the command is executed by the processor,
  the processor is configured to calculate a measurement value of the concentration based on the signal,
  the processor is configured to display at least one of a waveform corresponding to the signal and the measurement value on the displaying section,
  the sensor is configured such that the sensor is located at an ex vivo portion of the tube when the respiratory circuit is connected to a patient for ventilation and the sensor is operated,
  the processor is configured to extract a high-frequency component having a frequency which is higher than a predetermined value, from the signal, and
  the processor is configured to determine if the high-frequency oscillatory ventilation satisfies a desired waveform based on the high-frequency component.

18. The gas monitoring apparatus according to claim 17, further comprising a notifying section that provides a notification if the processor determines that the high-frequency oscillatory ventilation does not satisfy the desired waveform.

19. The gas monitoring apparatus according to claim 17, wherein,
  the processor is configured to display a measurement value of the concentration which is obtained after an end of sustained inflation of the lungs, as a feature value.

20. The gas monitoring apparatus according to claim 17, wherein
  the processor is configured to calculate the measurement value of the concentration by acquiring a moving average of a plurality of peak values of the signal contained in a predetermined period of time.

21. The gas monitoring apparatus according to claim 17, wherein the sensor includes:
  a light emitter that is located so as to emit a light beam toward the ex vivo portion of the tube, and
  a light detector that is located so as to receive the light beam after passing through the ex vivo portion.

22. A gas monitoring apparatus for artificial ventilation, the gas monitoring apparatus communicable with a sensor that is configured to produce a signal corresponding to a concentration of a predetermined gas in a tube in a respiratory circuit of an artificial ventilator, wherein an inspiratory gas and an expiratory gas both pass through the tube, the inspiratory gas passing in a first direction and the expiratory gas passing in a second direction opposite to the first direction, the gas monitoring apparatus comprising:
  a displaying section;
  a processor; and
  a memory that is configured to store a command which is readable by the processor, wherein,
  when, during high-frequency oscillatory ventilation performed by the artificial ventilator, the command is executed by the processor,
  the processor is configured to calculate a measurement value of the concentration based on the signal,
  the processor is configured to display at least one of a waveform corresponding to the signal and the measurement value on the displaying section,
  the sensor is configured such that the sensor is located at an ex vivo portion of the tube when the respiratory circuit is connected to a patient for ventilation and the sensor is operated,
  the processor is configured to extract a low-frequency component having a frequency which is lower than a predetermined value, from the signal, and
  in a case where the low-frequency component satisfies a predetermined condition, the processor is configured to produce a signal for causing the artificial ventilator to perform low-frequency ventilation.

23. The gas monitoring system according to claim 22, wherein the processor is configured to detect spontaneous respiration of the patient to whom the artificial ventilator is connected, based on the low-frequency component.

* * * * *

UNITED STATES PATENT AND TRADEMARK OFFICE
CERTIFICATE OF CORRECTION

| | | |
|---|---|---|
| PATENT NO. | : 11,833,296 B2 | Page 1 of 1 |
| APPLICATION NO. | : 16/014564 | |
| DATED | : December 5, 2023 | |
| INVENTOR(S) | : Toshiki Aoki | |

It is certified that error appears in the above-identified patent and that said Letters Patent is hereby corrected as shown below:

On the Title Page

Item (57); Line 11, "processor is to configured to" should read -- processor is configured to --

In the Specification

Column 3, Line 41, "term in 'can communicate'" should read -- term 'can communicate' --

Column 8, Line 60, "of to the high-frequency" should read -- of the high-frequency --

Signed and Sealed this
Twelfth Day of November, 2024

Katherine Kelly Vidal
*Director of the United States Patent and Trademark Office*